United States Patent [19]

Yokoyama et al.

[11] Patent Number: 5,034,212
[45] Date of Patent: Jul. 23, 1991

[54] METHOD OF IMAGING USING A RADIOACTIVE GLUCOSAMINE DERIVATIVE

[75] Inventors: Akira Yokoyama, Shiga; Yasuhiro Magata, Kyoto, both of Japan

[73] Assignee: Nihon Medi-Physics Co., Ltd., Hyogo, Japan

[21] Appl. No.: 552,196

[22] Filed: Jul. 13, 1990

[30] Foreign Application Priority Data

Jul. 13, 1989 [JP] Japan .................................. 1-181502

[51] Int. Cl.$^5$ ............................................ A61K 49/02
[52] U.S. Cl. ......................................... 424/1.1; 424/9
[58] Field of Search ..................... 424/1.1, 9; 536/18.4

[56] References Cited

PUBLICATIONS

Magata, Y. et al, Collection of Abstracts of Lectures to be Given at the 109th Annual Assembly of Pharmaceutical Society of Japan, p. 163, col. 5N 11-2 (3/1/89).
Bertoni, J. M. et al, Chemical Abstracts, 100: 117240C (Apr. 1984).

Saji, H. et al, Journal of Nuclear Medicine, vol. 29, pp. 928, 929, No. 787 (May 1988).

Primary Examiner—John S. Maples

[57] ABSTRACT

A radioactive diagnostic agent which comprises as an active ingredient a glucosamine derivative of the formula:

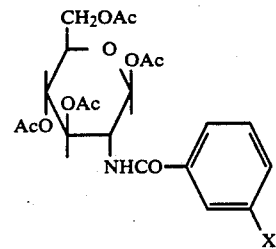

wherein Ac is an acetyl group and X is a radioactive iodine atom.

2 Claims, 2 Drawing Sheets

TLC Analysis
(silica gel plate; chloroform/methanol = 7/3)

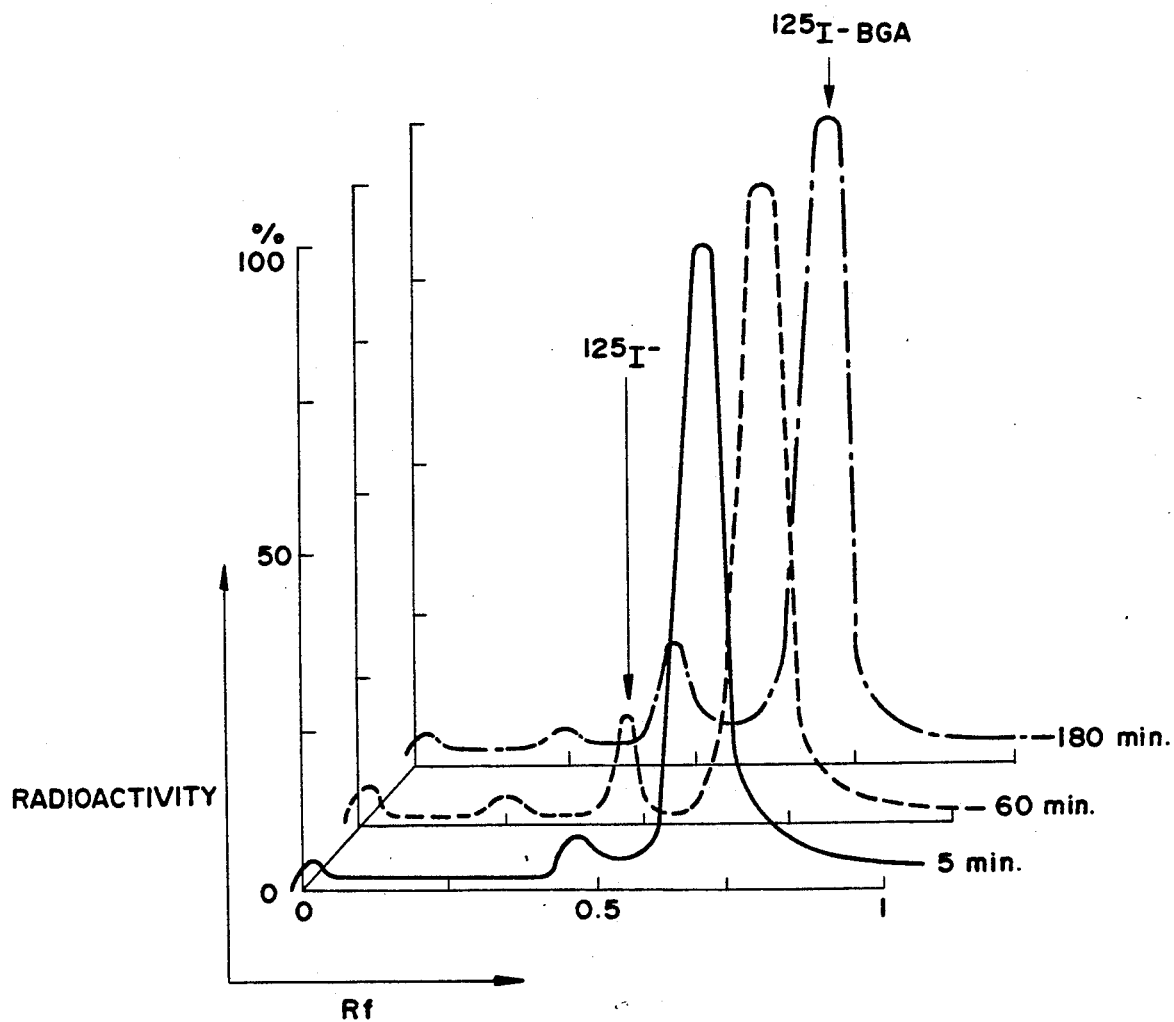

METHOD OF IMAGING USING A RADIOACTIVE GLUCOSAMINE DERIVATIVE

The present invention relates to a radioactive diagnostic agent. More particularly, it relates to a radioactive diagnostic agent comprising a radioactive iodine-labeled glucosamine derivative, which is useful for measurement of the capability of glucose transportation or glucose phosphorylation in various tissues and organs.

Since glucose is a major energy source in brain, heart, tumor, etc., tracing of its dynamic variation is considered to be useful for diagnosis of tissues and organs. Based on this consideration, there is developed $^{18}$F-labeled deoxyglucose ($^{18}$F-FDG), which is obtainable from glucose by substitution of the hydroxyl group at the 2-position with fluorine-18 (B. M. Gallagher et al.: J. Nucl. Med., 19, 1154 (1978)). Said $^{18}$F-FDG shows the same behavior in a living body and passes through a cell membrane into a cell according to the glucose carrier system. It is phosphorylated at the 6-position by the action of hexokinase inside the cell and is stored therein. Thus, $^{18}$F-FDG is a radioactive medicine developed for the purpose of nuclear medical diagnosis based on the dynamic function of glucose and admitted to be useful for diagnosis of local function of brain or heart, detection of tumor, judgement of malignancy, etc.

With respect to measurement of the local circulation metabolism in brain, it is observed that in normal cases, the blood stream, the oxygen consumption and the glucose consumption are all high in the gray matter where nerve cells are abundant and low in the white matter. Thus, coincidence is recognized between the blood stream and the metabolism. In view of this fact, attempt is also made to measure not the metabolism of glucose or the like but the blood stream, which is assumed to reflect the metabolism. A typical example in this respect is $^{123}$I-labeled amphetamine derivative, which passes through a blood-brain barrier and is retained in a brain for a period of time sufficient to accomplish nuclear medical examination. It is therefore used for measurement of the local blood stream in brain.

Since fluorine-18 used for $^{18}$F-FDG, with which the glucose metabolism can be measured, is a positron-emitting nuclide, a special imaging method such as positron-emission tomography (PET) is needed for the radioactive diagnosis with such nuclide. Also, fluorine-18 has such a short half life time as 109 minutes, restriction on time is unavoidable for the transportation and supply between the manufacture at a pharmaceutical plant and the use in a medical institution.

Because of the above reasons, the appearance of a substance which is labeled with a single photon-emitting nuclide, has a broader use and makes it possible to measure—the metabolism itself is demanded.

Positron nuclides such as carbon-11, nitrogen-13 and oxygen-15 are usual elements, which constitute metabolites themselves, and therefore can be used for labeling of metabolites without the material modification of their structure. To the contrary, single photon emitting nuclides as technetium-99 and iodine-123 are unusual elements to a living body, and therefore labeling of metabolites with such elements results in great change of their properties.

Due to the above reason, consideration was made on not tracing the metabolism itself but evaluating the function correlated to the metabolism, and according to this consideration, development of radioactive medicines was attempted. Thus, study was made on radioactive medicines which can evaluate the function correlated to the glucose metabolism for the capability of glucose transportation and glucose phosphorylation with hexokinase, and taking into consideration the facts that N-acyl derivatives of glucosamine participate in the reaction with hexokinase and that the glucose derivative wherein radioactive iodine is directly introduced into the carbon chain is unstable to produce deiodization, there was designed N-m-iodobenzoyl-D-glucosamine (BGA) in which the bonding of iodine is stable.

From the results of the body distribution of BGA in mouse, it was understood that BGA is low in stomach accumulation as the index of deiodization and thus stable in a body. It was also understood that BGA is not phosphorylated with hexokinase but shows a nonantagonistic inhibition to the phosphorylation of glucose and an antagonistic inhibition to the ATP action. On the other hand, however, it was observed that the disappearance of the radioactivity of BGA from brain is parallel to the blood clearance. Thus, BGA can hardly pass through the blood-brain barrier (BBB) in vivo and is therefore difficult to be transferred into brain.

An extensive study has been made seeking a radioactive medicine which can be transferred easily through the blood-brain barrier into brain and retained there for a period of time sufficient to diagnosis so as to make possible the evaluation of the capability of glucose phosphorylation with esterase, it has now been found that esterification of BGA results in enhancing its lipophylic property so that the esterified product can pass easily through the blood-brain barrier. Among various esterification products, the acetylation product is quite advantageous, because after taken up into brain, it is converted into BGA, on which the capability of glucose phosphorylation can be evaluated, by the action of brain esterase and retained in brain over a period of time sufficient for examination, e.g. imaging. The present invention is based on the above finding.

SUMMARY OF THE INVENTION

According to the present invention, there is provided a radioactive diagnostic agent which comprises as an active ingredient a glucosamine derivative of the formula:

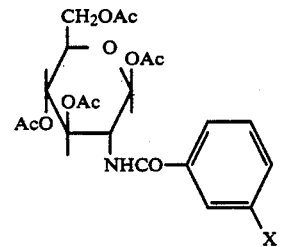

wherein Ac is an acetyl group and X is a radioactive iodine atom.

According to the present invention, there is also provided a method for evaluation of the capability of glucose phosphorylation in the brain, which comprises administering said radioactive diagnostic agent into a mammal intravenously and after a sufficient time, imaging.

BRIEF DESCRIPTION OF THE DRAWINGS

FIG. 1B is a graph of data for Example 6 for TLC analysis of mouse blood homogenate after $^{125}$I-ABGA administration.

DETAILED DESCRIPTION

Figure 1A:
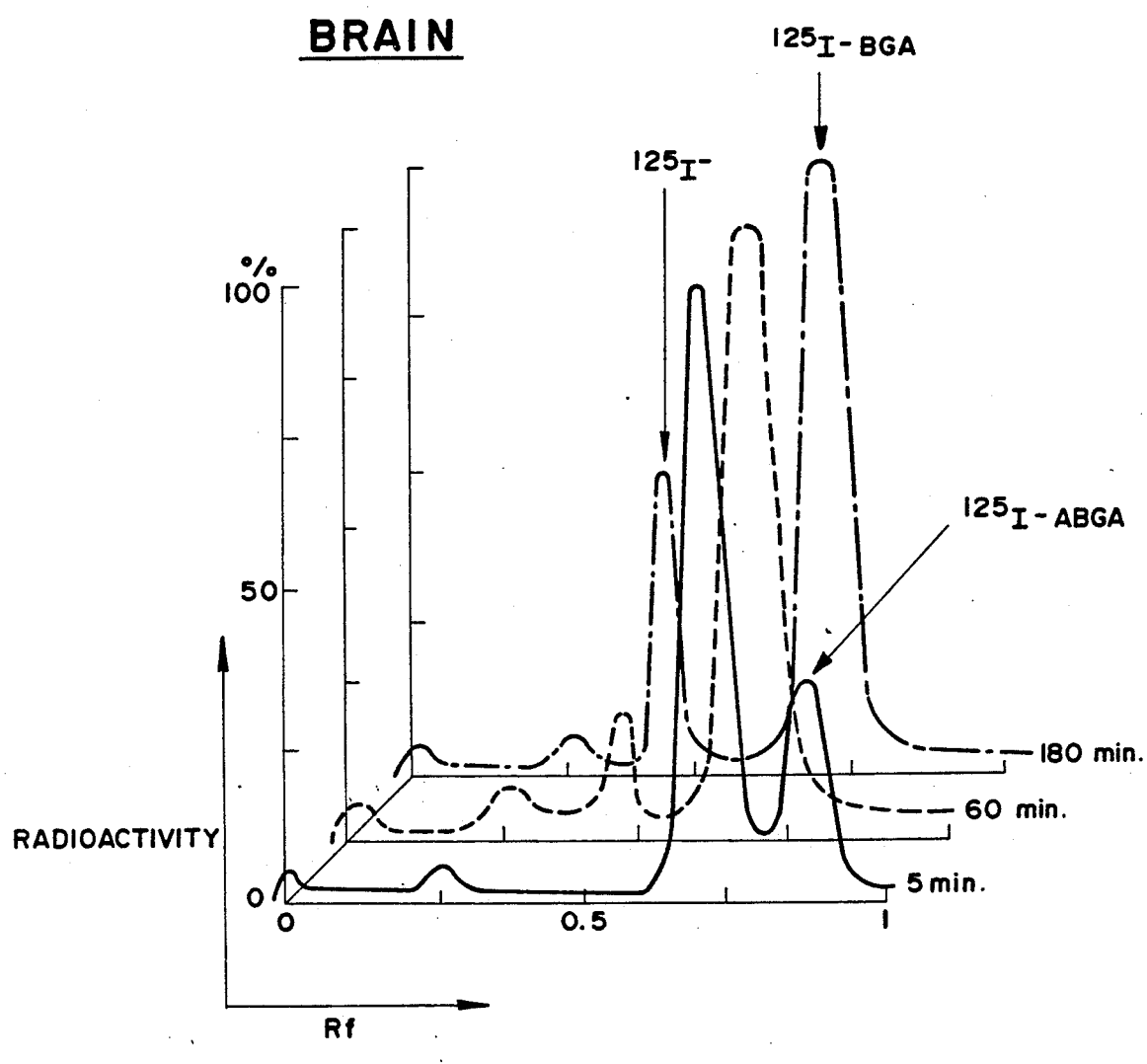
FIG. 1A is a graph of data for Example 6 for TLC analysis of mouse brain homogenate after $^{125}$I-ABGA administration.

As understood from the above formula, the glucosamine derivative of the invention is acetylated at the hydroxyl groups of the glucose moiety in BGA. It is deacetylated by the action of an esterase in brain to give BGA, on which the capability of glucose phorphorylation can be evaluated and which can be retained in brain.

For the practical use, the glucosame derivative of the invention is dissolved into a pharmaceutically acceptable liquid diluent such as physiologically saline solution and injected intravenously into a mammalian body such as a human body usually at a dose of 1 to 20 mCi, preferably 3 to 10 mCi. After a sufficient time for transfer into brain and deacetylation (usually several hours), imaging is carried by the use of a gamma-camera.

Practical and presently preferred embodiments of the invention are illustratively shown in the following examples.

EXAMPLE 1

Preparation of N-(m-iodobenzoyl)-1,3,4,6-tetra-O-acetyl-D-glucosamine

To a solution of glucosamine hydrochloride (9 g; 0.042 mol) in 1N sodium hydroxide solution (42.3 ml) anisaldehyde (5.76 g; 0.042 mol) was added, and the resultant mixture was stirred at room temperature for 3 hours and then cooled at 0° C. for 30 minutes. The precipitated crystals were collected by filtration, washed with cold water and a mixture of ethanol and ether (1:1 by volume) in order to give N-p-methoxybenzylidene-D-glucosamine (9.6 g).

The thus obtained N-p-methoxybenzylidene-D-glucosamine (5 g; 0.017 mol) was suspended in acetic anhydride (15 ml), and dry pyridine (27 ml) was added thereto while cooling with ice, followed by stirring for 5 minutes. The resultant mixture was allowed to stand at room temperature for 24 hours, admixed with ice water (85 ml) and again allowed to stand for 2 hours. The precipitated crystals were collected by filtration, washed with cold water and recrystallized from methanol to give N-p-methoxy-benzylidene-1,3,4,6-tetra-O-acetyl-D-glucosamine (7.1 g).

The above obtained N-p-methoxybenzylidene-1,3,4,6-tetra-O-acetyl-D-glucosamine (5 g; 0.010 mol) was dissolved in acetone (25 ml) and hot, conc. hydrochloric acid (1 ml) was added thereto, and the resultant mixture was allowed to stand for 24 hours. The precipitated crystals were collected by filtration and washed with cold ether. The resulting crystals were suspended in 2M sodium acetate solution (50 ml) and extracted with a three time volume of chloroform, followed by crystallization to give 1,3,4,6-tetra-O-acetyl-D-glucosamine (2.9 g).

A mixture of m-iodobenzoic acid (1.6 g; 6.45×10$^{-3}$ mol) and thionyl chloride (10 ml) was stirred at 65° C. for 24 hours, benzene was added thereto, and excessive thionyl chloride was removed by distillation under reduced pressure. The thus prepared m-iodobenzoyl chloride was dissolved in benzene (2 ml), and a solution of 1,3,4,6-tetra-O-acetyl-D-glucosamine (2 g; 5.76×10$^{-3}$ mol) in benzene (10 ml) and pyridine (2 ml) was added thereto, followed by stirring for 48 hours. The resulting mixture was neutralized with 0.1N hydrochloric acid and extracted with chloroform, followed by crystallization from methanol to give N-(m-iodobenzoyl)-1,3,4,6-tetra-O-acetyl-D-glucosamine (ABGA) (1.50 g).

Identification of the product to ABGA was made by the analytical results as set forth below.

Elementary analysis for $C_{21}H_{24}O_{10}NI$ (%): Calcd.: C, 43.69; H, 4.19; N, 2.43. Found: C, 43.67; H, 4.21; N, 2.33.

NMR (CDCl$_3$) (TMS) ppm: 2.04 (s, 3H), 2.08 (s, 6H), 2.11 (s, 3H), 3.90 (ddd, 1H), 4.17 (dd, 1H), 4.30 (dd, 1H), 4.58 (ddd, 1H), 5.22 (t, 1H), 5.36 (dd, 1H), 5.80 (d, 1H), 6.57 (d, 1H), 7.13 (t, 1H), 7.65 (dt, 1H), 7.83 (dt, 1H), 8.06 (t, 1H).

EXAMPLE 2

Labeling with Radioactive Iodine

N-(m-Iodobenzoyl)-1,3,4,6-tetra-O-acetyl-D-glucosamine (ABGA) (4 mg) was dissolved in a mixture of ethanol (0.5 ml) and distilled water (0.5 ml), cupric sulfate solution, ammonium sulfate solution and $^{125}$I-NaI (1 mCi) were added thereto, and the resultant mixture was heated at 85° C. for 3 hours. After cooling, the reaction mixture was subjected to silica gel column chromatography using a mixture of chloroform and methanol (8:2 by volume) for removal of the decomposition product and the unreacted $^{125}$I-labeled N-(m-iodobenzoyl)-1,3,4,6-tetra-O-acetyl-D-glucosamine ($^{125}$I-ABGA) (0.81 mCi). Yield, 81.8±9.9 %.

EXAMPLE 3

Lipophilic Property of $^{125}$I-ABGA

To a mixture of octanol (3 ml) and phosphate buffer (PBS) (3 ml), $^{125}$I-ABGA as obtained in Example 2 was added, followed by stirring and allowing to stand. The radioactivity of each layer was measured, and the distribution ratio was determined. The results are shown in Table 1, from which it is understood that $^{125}$I-ABGA is lypophilic.

TABLE 1

| | Distribution Ratio of $^{125}$I-ABGA in PBS and Octanol | | |
|---|---|---|---|
| | pH | | |
| | 7.0 | 7.4 | 8.10 |
| Distribution rati | 189.0 (±11.4) | 193.8 (±5.1) | 206.5 (±7.6) |

EXAMPLE 4

Stability of $^{125}$I-ABGA

A solution of $^{125}$I-ABGA in dimethylsulfoxide was added to a buffer of pH 5, 7 or 9 and incubated at 37° C. for a certain period of time. The reaction mixture was analyzed by thin layer chromatography, and the results are shown in Table 2, from which it is understood that $^{125}$I-ABGA is hydrolyzed to BGA with deiodization at high pH, while it is stable (i.e. neither hydrolyzed nor deiodized) even after 3 hours at other pH.

TABLE 2

| Peak component | Stability of $^{125}$I-ABGA | | | | | | | | |
|---|---|---|---|---|---|---|---|---|---|
| | Time (min) | | | | | | | | |
| | 15 | | | 60 | | | 180 | | |
| | pH | | | | | | | | |
| | 5 | 7 | 9 | 5 | 7 | 9 | 5 | 7 | 9 |
| ABGA | 99.1 | 99.9 | 53.9 | 98.5 | 99.3 | 25.5 | 98.4 | 97.8 | 2.2 |
| I$^-$ | 0 | 0 | 10.2 | 0 | 0 | 19.6 | 0 | 0.9 | 31.1 |
| Others | 0 | 0 | 31.5 | 0 | 0 | 49.0 | 0 | 0 | 57.5 |

EXAMPLE 5

Enzymatic Deesterification of $^{125}$I-ABGA

Swine liver esterase (100 U) was added to phosphate buffer (pH 7.4), and $^{125}$I-ABGA (50 kBq) was added thereto, followed by incubation at 37° C. for a certain period of time. The reaction mixture was sampled, and ethanol was added thereto, followed by centrifugation. The supernatant was subjected to thin layer chromatography, and the results are shown in Table 3, from which it is understood that $^{125}$I-ABGA is deesterified in a very short time to give N-m-iodobenzoyl-D-glucosamine (BGA).

TABLE 3

| | Proportion of Peak Components obtained by Enzymatic Deesterification | | |
|---|---|---|---|
| | Time (min) | | |
| Component | 10 | 60 | 180 |
| ABGA | 0 | 0 | 0 |
| BGA | 87.3 ± 3.1 | 54.5 ± 3.7 | 7.2 ± 2.2 |
| I$^-$ | 0.9 ± 0.5 | 6.5 ± 0.5 | 33.4 ± 1.6 |
| Others | 10.6 ± 2.9 | 33.7 ± 2.4 | 42.9 ± 0.4 |

EXAMPLE 6

Behavior of $^{125}$I-ABGA in Mouse $^{125}$I-ABGA was injected into ddY strain male mice at the tail vein, and after a certain period of time, the mice were sacrificed. The blood was collected from the heart, and the brain was taken out. The blood and the brain were respectively admixed with 5% trichloroacetic acid (1 ml), homogenized and centrifuged at 3,000 rpm and at 0° C. for 10 minutes. The supernatant was analyzed by thin layer chromatography using a mixture of chloroform and methanol (7:3 by volume) as a developing solvent. The results are shown in FIGS. 1A and 1B of the accompanying drawings. In FIGS. 1A and 1B showing respectively the analytical results on the brain homogenate and the blood homogenate, the solid line, the dotted line and the solid-dot mixed line represent respectively the ones of 5 minutes, 60 minutes and 180 minutes after the administration.

From FIGS. 1A and 1B, it is understood that the peaks of ABGA and BGA appear in brain 5 minutes after the administration. The peak of ABGA decreases with the lapse of time. Thus, ABGA is transferred to brain at the initial stage of administration and thereafter deesterified, whereby it behaves as BGA.

EXAMPLE 7

Body Distribution of $^{125}$I-ABGA in Mouse $^{125}$I-ABGA was injected into ddY strain male mice at the tail vein, and the body distribution was determined in the same manner as in Example 6. The results are shown in Table 4.

From Table 4, it is understood that ABGA shows rapid clearance from the blood and, in comparison with BGA, higher uptake in the brain. It gives retention in the brain and indicates the increase of the brain/blood ratio with the lapse of time.

TABLE 4

| | Body distribution of $^{125}$I-ABGA in mouse (% dose/g organ) | | | | | |
|---|---|---|---|---|---|---|
| | Time elapsed (min) | | | | | |
| Organ | 2 | 5 | 15 | 30 | 60 | 180 |
| Blood | 5.16 ± 0.97 | 7.16 ± 0.13 | 6.64 ± 0.31 | 4.16 ± 2.42 | 3.67 ± 0.40 | 0.91 ± 0.55 |
| Liver | 15.32 ± 4.43 | 12.85 ± 1.71 | 7.66 ± 0.86 | 5.82 ± 0.64 | 4.94 ± 0.90 | 2.25 ± 1.44 |
| Kidney | 14.87 ± 2.31 | 11.39 ± 3.08 | 7.00 ± 0.49 | 6.37 ± 3.04 | 3.81 ± 0.75 | 1.08 ± 0.67 |
| Stomach | 1.87 ± 0.68 | 0.59 ± 0.23 | 1.88 ± 0.52 | 1.86 ± 0.13 | 1.74 ± 0.83 | 1.27 ± 0.80 |
| Intestine | 3.94 ± 1.19 | 4.58 ± 0.60 | 5.89 ± 0.47 | 6.26 ± 0.96 | 6.88 ± 0.53 | 4.60 ± 2.84 |
| Pancreas | 4.54 ± 1.03 | 4.40 ± 0.28 | 3.16 ± 0.30 | 2.59 ± 0.13 | 2.10 ± 0.34 | 0.76 ± 0.35 |
| Heart | 4.88 ± 0.97 | 4.45 ± 0.52 | 3.35 ± 0.27 | 2.69 ± 0.20 | 1.87 ± 0.37 | 0.75 ± 0.34 |
| Brain | 0.53 ± 0.14 | 0.55 ± 0.11 | 0.47 ± 0.06 | 0.43 ± 0.02 | 0.33 ± 0.05 | 0.19 ± 0.08 |

The radioactive diagnostic agent of the invention comprising the glucosamine derivative passes through the blood-brain barrier and is transferred into brain. In brain, it is converted into BGA by the action of esterase. Accordingly, it is useful for evaluation of the capability of glucose phosphorylation, especially for diagnosing the diseases in various tissues and organs such as brain, heart, tumor, etc., which are correlated to the glucose metabolism.

What is claimed is:

1. A method for evaluation of the capability of glucose phosphorylation in a brain, which comprises an administering an effective amount of a radioactive diagnostic agent into a mammal intravenously and, after a sufficient time that the glucosamine derivative in the radioactive diagnostic agent is transferred into the brain and converted into the corresponding deacetylated product, imaging; said radioactive diagnostic agent comprising as an active ingredient a glucosamine derivative of the formula:

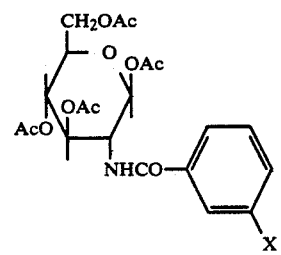

wherein Ac is an acetyl group and X is a radioactive iodine atom.

2. The method of claim 1 wherein X in said glucosamine derivative is selected from the group consisting of I-123, I-125, I-131 and I-132.

* * * * *